United States Patent
Stebbins et al.

(10) Patent No.: US 12,226,506 B2
(45) Date of Patent: Feb. 18, 2025

(54) COSMETIC COMPOSITION COMPRISING NATURAL EMULSIFIERS AND THIOPYRIDINONE COMPOUNDS

(71) Applicant: L'OREAL, Paris (FR)

(72) Inventors: Nicholas David Stebbins, Rahway, NJ (US); David Chan, Oradell, NJ (US)

(73) Assignee: L'OREAL, Paris (FR)

( * ) Notice: Subject to any disclaimer, the term of this patent is extended or adjusted under 35 U.S.C. 154(b) by 53 days.

(21) Appl. No.: 17/844,930

(22) Filed: Jun. 21, 2022

(65) Prior Publication Data

US 2023/0404883 A1    Dec. 21, 2023

(51) Int. Cl.
| | |
|---|---|
| *A61K 8/49* | (2006.01) |
| *A61K 8/06* | (2006.01) |
| *A61K 8/73* | (2006.01) |
| *A61K 8/86* | (2006.01) |
| *A61Q 19/02* | (2006.01) |

(52) U.S. Cl.
CPC .......... *A61K 8/4933* (2013.01); *A61K 8/062* (2013.01); *A61K 8/73* (2013.01); *A61K 8/86* (2013.01); *A61Q 19/02* (2013.01); *A61K 2800/524* (2013.01)

(58) Field of Classification Search
None
See application file for complete search history.

(56) References Cited

U.S. PATENT DOCUMENTS

2013/0315847 A1* 11/2013 Marat .................. A61K 8/4926
                                                                            424/59
2021/0401715 A1   12/2021 Faig

FOREIGN PATENT DOCUMENTS

| CN | 106074663 B | 8/2019 | |
| FR | 3118871 A1 | 7/2022 | |
| WO | WO-2009148206 A1 * | 12/2009 | ............. A61K 31/07 |
| WO | 2012080075 A1 | 6/2012 | |
| WO | 2022079122 A1 | 4/2022 | |
| WO | 2022138471 A1 | 6/2022 | |

OTHER PUBLICATIONS

Search Report of corresponding application FR 2211483, mailed Jul. 7, 2023, 2 pages.
International Search Report of corresponding International Application PCT/US2023/025681 mailed Oct. 9, 2023, 3 pages.

* cited by examiner

*Primary Examiner* — Nannette Holloman
(74) *Attorney, Agent, or Firm* — Laetitia Leproust; Robert Klemz

(57) ABSTRACT

The instant disclosure relates to oil-in-water compositions comprising: (i) compound of thiopyridinone type; (ii) a blend of natural emulsifiers; wherein the oil-in-water cosmetic composition is physically stable.

19 Claims, No Drawings

COSMETIC COMPOSITION COMPRISING NATURAL EMULSIFIERS AND THIOPYRIDINONE COMPOUNDS

FIELD OF THE DISCLOSURE

The present disclosure relates to cosmetic compositions comprising a combination of natural emulsifiers and compound of thiopyridinone type.

BACKGROUND OF THE DISCLOSURE

It has always been an ultimate target of the cosmetic filed to deliver products with skin benefits such as hydration, moisturizing, anti-aging, whitening, cleansing, and so on. Whitening and brightening of the skin is always high interest of the consumers, especially those who have a dark or dull skin tone. Unfortunately, at various periods of their life, some people see the appearance on their skin, and more in particular on the hands, of darker and/or more colored spots, which give the skin heterogeneity. These spots are in particular due to a high concentration of melanin in the keratinocytes located at the surface of the skin.

Accordingly, there is a need in the art for cosmetic composition that offers stable formulation that includes actives for brightening skin and reducing dark spots, or a combination of these.

SUMMARY OF THE DISCLOSURE

The present disclosure relates to stable oil-in-water cosmetic compositions comprising compound of thiopyridinone type and a blend of natural emulsifiers. The cosmetic compositions have low viscosity. The compositions described in the instant disclosure are unique in comparison to other traditional oil-in-water compositions that contain emulsifiers containing PEG groups that offer the greatest flexibility and stability when formulating because of the oligomeric nature of the molecules. However, with concerns about naturality obtaining emulsion stability using more naturally-derived molecules can prove useful. In contrast to mainly PEG-based and other synthetic emulsifiers, natural-based emulsifiers are in far fewer number. Moreover, they do not have the same advantages as the aforementioned oligomeric emulsifiers. Natural emulsifiers are often more difficult to formulate with, but they have benefits of naturality.

The inventors have discovered that the inclusion of a combination of compound of thiopyridinone type (I) or (I') and a blend of natural emulsifiers surprisingly stabilize oil-in-water cosmetic compositions. The oil-in-water cosmetic composition typically include:

i) at least one compound selected from compounds of formula (I) and tautomer of formula (I') herein below; and their optical isomers, racemates, and/or solvates such as hydrates, alone or as a mixture:

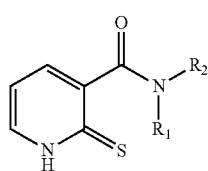

(I)

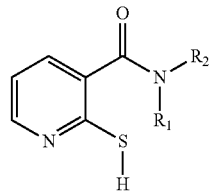

(I')

In which Formulas (I) and (I')
$R_1$ denotes a radical chosen from:
  a) a hydrogen atom;
  b) a saturated linear $C_1$-$C_{10}$ or branched $C_3$-$C_{10}$ alkyl group optionally substituted with one or more groups, which may be identical or different, chosen from:
    i) —O—$R_3$
    ii) —S—$R_3$;
$R_2$ denotes a radical chosen from:
  a) a hydrogen atom;
  b) a saturated hydrocarbonated group linear $C_1$-$C_{12}$ or branched $C_3$-$C_{12}$ or cyclic $C_3$-$C_8$, optionally substituted with one or more groups, which may be identical or different, chosen from:
    i) —O—$R_3$
    ii) —S—$R_3$
    iii) —C(O)—O—$R_3$;
  iv) a $C_5$-$C_{12}$ aryl group optionally substituted with one or more hydroxyls and/or with one or more $C_1$-$C_8$ alkoxy radicals;
  c) a $C_5$-$C_{12}$ aryl group optionally substituted with one or more hydroxyls and/or with one or more $C_1$-$C_8$ alkoxy radicals
$R_3$ denotes a radical chosen from:
  a) a hydrogen atom;
  b) a saturated linear $C_1$-$C_{10}$ or branched $C_3$-$C_{10}$ alkyl group;
ii) at least two or more natural emulsifiers; and
wherein the oil-in-water cosmetic composition is physically stable.

In some embodiments, the compound i) is typically present in the cosmetic compositions in an amount of from about 0.01 to about 10 wt. %, based on the total weight of the cosmetic composition. In some cases, the amount of compound i) is present in an amount of from about 0.1 to about 5 wt. %, based on the total weight of the cosmetic composition. In some embodiments, the compound i) is typically present in the cosmetic compositions in an amount of from about 0.5 to about 3 wt. %, based on the total weight of the cosmetic composition.

In some embodiments, the cosmetic compositions may include a blend of at least two or more natural emulsifiers that have intermediate to high HLB. In some embodiments, the cosmetic compositions may include a blend of at least two or more natural emulsifiers that have a HLB from about 10 to about 15. In one or more embodiments, the at least two or more natural emulsifiers has a HLB from about 10 to about 15. In some embodiments, the cosmetic composition may include at least two or more natural emulsifiers selected from the group consisting of inulin lauryl carbamate, C12-20 Alkyl Glucoside, Cetearyl Alcohol (and) Cetearyl Glucoside, APGs, Arachidyl Alcohol (And) Behenyl Alcohol (And) Arachidyl Glucoside, Polyglyceryl-3 Methylglucose Distearate, Glyceryl citrate stearate, sucrose and glucose esters and ethers, amino acid-based emulsifier, Hydrogenated lecithin, lecithins, Sodium lauroyl glutamate, sodium stearoyl glutamate and a mixture thereof. In one embodiment, the at least two or more natural emulsifiers is inuline carbamate.

In some embodiments, the at least two or more natural emulsifiers are present from about 0.3 to about 6 wt. %, based on the total weight of the cosmetic composition.

In one or more embodiments, the sucrose have an intermediate to high HLB.

In some embodiments, the cosmetic compositions may include non-natural emulsifiers.

In some embodiments, the cosmetic compositions may include one or more thickening polymers.

In some embodiments, the cosmetic compositions may include one or more fatty compounds.

In some embodiments, the cosmetic composition has a low viscosity.

In some embodiments, the cosmetic compositions may include inulin lauryl carbamate that can be present from about 0.2 wt. % to about 3 wt. %, based on the total weight of the cosmetic composition.

In one or more embodiments, the cosmetic composition may have a pH ranging from about 4.5 to about 6.5, preferably from about 5 to about 6.

In one or more embodiments, the cosmetic composition may include:
i) from about 0.01 to about 10 wt. % of at least one compound selected from compounds of formula (I) and tautomer of formula (I') herein below; and their optical isomers, racemates, and/or solvates such as hydrates, alone or as a mixture:

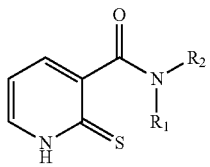
(I)

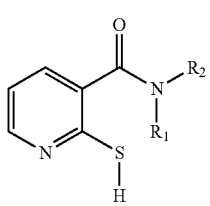
(I')

In which Formulas (I) and (I'):
$R_1$ denotes a radical chosen from:
  a) a hydrogen atom;
  b) a saturated linear $C_1$-$C_{10}$ or branched $C_3$-$C_{10}$ alkyl group optionally substituted with one or more groups, which may be identical or different, chosen from:
    i) —O—$R_3$
    ii) —S—$R_3$;
$R_2$ denotes a radical chosen from:
  a) a hydrogen atom;
  b) a saturated hydrocarbonated group linear $C_1$-$C_{12}$ or branched $C_3$-$C_{12}$ or cyclic $C_3$-$C_8$, optionally substituted with one or more groups, which may be identical or different, chosen from:
    i) —O—$R_3$
    ii) —S—$R_3$
    iii) —C(O)—O—$R_3$;
  iv) a $C_5$-$C_{12}$ aryl group optionally substituted with one or more hydroxyls and/or with one or more $C_1$-$C_8$ alkoxy radicals;
  c) a $C_5$-$C_{12}$ aryl group optionally substituted with one or more hydroxyls and/or with one or more $C_1$-$C_8$ alkoxy radicals
$R_3$ denotes a radical chosen from:
  a) a hydrogen atom;
  b) a saturated linear $C_1$-$C_{10}$ or branched $C_3$-$C_{10}$ alkyl group;
ii. about 0.5 to about 2 wt. % of at least two or more natural emulsifiers that are elected from the group consisting of inulin lauryl carbamate, C12-20 Alkyl Glucoside, Cetearyl Alcohol (and) Cetearyl Glucoside, APGs, Arachidyl Alcohol (And) Behenyl Alcohol (And) Arachidyl Glucoside, Polyglyceryl-3 Methylglucose Distearate, Glyceryl citrate stearate, sucrose and glucose esters and ethers, amino acid-based emulsifier, Hydrogenated lecithin, lecithins, Sodium lauroyl glutamate, sodium stearoyl glutamate and a mixture thereof, wherein the weight percentages are based on the total weight of the cosmetic composition.

The cosmetic compositions can be used in a method that comprises applying the cosmetic compositions to the skin of humans.

It was proven that natural emulsifiers were able to effectively stabilize an o/w emulsion containing the newly developed raw material, compound of thiopyridinone type, with the same effectiveness as PEG-based emulsifiers.

These and other aspects of the disclosure are set out in the appended claims and described in greater detail in the detailed description of the disclosure.

This disclosure describes exemplary embodiments in accordance with the general inventive concepts and is not intended to limit the scope of the disclosure in any way. Indeed, the disclosure as described in the specification is broader than and unlimited by the exemplary embodiments set forth herein, and the terms used herein have their full ordinary meaning.

DETAILED DESCRIPTION OF THE DISCLOSURE

The present disclosure relates to cosmetic compositions typically including at least one compound corresponding to the following formula (I) or (I'), referred to as "compound of thiopyridinone type".

The present disclosure provides cosmetic compositions that are unique in comparison to conventional cosmetic compositions because they contain an association of compound of thiopyridinone type and a blend of natural emulsifiers, that show to be stable oil-in-water cosmetic compositions.

The cosmetic compositions of the instant disclosure typically include:
i) at least one compound selected from compounds of formula (I) and tautomer of formula (I') herein below; and their optical isomers, racemates, and/or solvates such as hydrates, alone or as a mixture

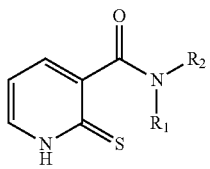

(I)

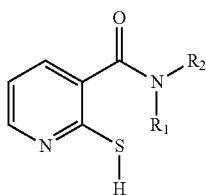

(I')

In which Formulas (I) and (I')

R$_1$ denotes a radical chosen from:
  a) a hydrogen atom;
  b) a saturated linear C$_1$-C$_{10}$ or branched C$_3$-C$_{10}$ alkyl group optionally substituted with one or more groups, which may be identical or different, chosen from:
     i) —O—R$_3$
     ii) —S—R$_3$;

R$_2$ denotes a radical chosen from:
  a) a hydrogen atom;
  b) a saturated hydrocarbonated group linear C$_1$-C$_{12}$ or branched C$_3$-C$_{12}$ or cyclic C$_3$-C$_8$, optionally substituted with one or more groups, which may be identical or different, chosen from:
     i) —O—R$_3$
     ii) —S—R$_3$
     iii) —C(O)—O—R$_3$;
     iv) a C$_5$-C$_{12}$ aryl group optionally substituted with one or more hydroxyls and/or with one or more C$_1$-C$_8$ alkoxy radicals;
  c) a C$_5$-C$_{12}$ aryl group optionally substituted with one or more hydroxyls and/or with one or more C$_1$-C$_8$ alkoxy radicals R$_3$ denotes a radical chosen from:
  a) a hydrogen atom;
  b) a saturated linear C$_1$-C$_{10}$ or branched C$_3$-C$_{10}$ alkyl group;
  ii) at least two or more natural emulsifiers; and wherein the oil-in-water cosmetic composition is physically stable.

The inventors have discovered that natural emulsifiers were able to effectively stabilize an o/w emulsion containing the newly developed raw material, compound of thiopyridinone type, with the same effectiveness as PEG-based emulsifiers.

Cosmetic formulations comprising the novel association that are appropriate for topical application to the skin include compositions having low viscosity such as lotion, serum, gel, gel cream.

The term "natural," as used herein refers to a compound or component that is obtained directly from the earth or soil or from plants or animals, via, if appropriate, one or more physical processes, such as grinding, refining, distillation, purification or filtration. A "natural emulsifier" could still be subjected to a synthetic process. For example, C$_{12}$-22 alkyl glucoside is not extracted from plants. It is made synthetically from C$_{12}$-22 alcohols (which are extracted and separated from natural sources) and glucose (which is from natural sources). It is still considered completely "natural" because it is comprised of 100% natural components, even though the end result is made synthetically.

The term "natural", as used herein is defined as having more than 80% w/w naturally occurring elements in the raw material. Generally, the % naturality of RM is equal to molecular weight of naturally-occurring portions of molecule divided by total molecular weight of molecule. For example, if we look at sucrose laurate as a general example, there are two components to synthesis this raw material: sucrose and lauric acid. The sucrose is 100% natural in that is extracted from sugar cane; thus 100% of carbons in the molecule are natural. Likewise, the lauric acid is 100% natural because it is derived from coconut; thus 100% of carbons in the molecule are natural. Even though a synthetic process is preformed to make sucrose laurate, 100% of the carbons that comprise the molecule came from natural sources.

Suitable components, such as those listed below, may be included or excluded from the formulations for the cosmetic compositions depending on the specific combination of other components, the form of the cosmetic compositions, and/or the use of the formulation (e.g., a lotion, a serum, gel, etc.).

Compounds Of Thiopyridinone Type

For the purposes of the instant disclosure, and unless otherwise indicated:
  a "saturated hydrocarbonated group linear C$_1$-C$_{12}$ or branched C$_3$-C$_{12}$" is equivalent to a "linear (C$_1$-C$_{12}$) alkyl or branched (C$_3$-C$_{12}$)alkyl group" which correspond to a saturated C$_1$-C$_{12}$ linear or branched C$_3$-C$_{12}$ hydrocarbon based group, and preferably C$_1$-C$_{10}$ linear or C$_3$-C$_1$a branched hydrocarbon based group, more preferably C$_1$-C$_6$ linear or C$_3$-C$_6$ branched hydrocarbon-based; Preferentially, the linear or branched groups may be chosen from methyl, ethyl, propyl, isopropyl, butyl, isobutyl and tert-butyl, pentyl, hexyl, heptyl, octyl, nonyl and decyl.
  More preferentially, the saturated linear or branched alkyl groups may be chosen from methyl, ethyl, propyl, isopropyl, butyl, isobutyl and tert-butyl, pentyl, hexyl, heptyl and octyl, such as methyl, ethyl, n-pentyl, n-nonyl, isobutyl.
  a saturated hydrocarbonated cyclic C$_3$-C$_8$ group is a mono or bicyclic cycloalkyl group containing from 3 to 8 carbon atoms especially is a monocyclic cycloalkyl group in C$_5$ to C$_7$ such as cyclohexyl group,
  an "alkoxy radical" is an alkyl-oxy radical for which the alkyl radical is a linear or branched C$_1$-C$_{16}$ and preferentially C$_1$-C$_8$ hydrocarbon-based radical;
  when the alkoxy group is optionally substituted, this implies that the alkyl group is optionally substituted as defined hereinabove;
  an "aryl" group represents a fused or non-fused monocyclic or bicyclic carbon-based group comprising from 5 to 12 carbon atoms, preferably from 6 to 10 carbon atoms, and in which at least one ring is aromatic; preferentially, the aryl radical is a phenyl, biphenyl, naphthyl, more preferably a phenyl group;
  the term "at least one" is equivalent to the term "one or more"; and
  the term "inclusive" for a range of concentrations means that the limits of that range are included in the defined range.

The salts of the compounds of formula (I), (I'), (II) or (II') as defined herein after comprise the conventional non-toxic salts of said compounds, such as those formed from organic or inorganic acid or from organic or inorganic base.

As salts of the compounds of formula (I), (I'), (II) or (II') mention may be made of: the salts obtained by addition of the compound of formula (I) or (II) to:
- a mineral base, such as sodium hydroxide, potassium hydroxide, calcium hydroxide, ammonium hydroxide, magnesium hydroxide, lithium hydroxide, and sodium, potassium or calcium carbonate or hydrogen carbonate for example;

or
- an organic base such as a primary, secondary or tertiary alkylamine, for example triethylamine or butylamine. This primary, secondary or tertiary alkylamine may comprise one or more nitrogen and/or oxygen atoms and may thus comprise, for example, one or more alcohol functions; mention may be made in particular of 2-amino-2-methylpropanol, ethanolamine, triethanolamine, 2-dimethylaminopropanol, 2-amino-2-(hydroxymethyl)-1,3-propanediol and 3-(dimethylamino) propylamine.

Mention may also be made of the salts of amino acids, for instance lysine, arginine, guanidine, glutamic acid and aspartic acid. Advantageously, the salts of the compounds of formula (I) or (II) (when it comprises a carboxy group) may be chosen from alkali metal or alkaline-earth metal salts such as sodium, potassium, calcium or magnesium salts and ammonium salts.
- as "organic or inorganic acid salt" is more particularly chosen from salts chosen from a salt derived from i) hydrochloric acid HCl, ii) hydrobromic acid HBr, iii) sulfuric acid $H_2SO_4$, iv) alkylsulfonic acids: Alk-S(O)$_2$OH such as methanesulfonic acid and ethanesulfonic acid; v) arylsulfonic acids: Ar—S(O)$_2$OH such as benzenesulfonic acid and toluenesulfonic acid; vi) citric acid; vii) succinic acid; viii) tartaric acid; ix) lactic acid; x) alkoxysulfinic acids: Alk-O—S(O)OH such as methoxysulfinic acid and ethoxysulfinic acid; xi) aryloxysulfinic acids such as tolueneoxysulfinic acid and phenoxysulfinic acid; xii) phosphoric acid $H_3PO_4$; xiii) acetic acid $CH_3C(O)OH$; xiv) triflic acid $CF_3SO_3H$; and xv) tetrafluoroboric acid $HBF_4$;
- The acceptable solvates of the compounds described in the instant disclosure comprise conventional solvates such as those formed during the preparation of said compounds owing to the presence of solvents. Mention may be made, by way of example, of the solvates due to the presence of water or of linear or branched alcohols, such as ethanol or isopropanol.
- The optical isomers are in particular, the enantiomers and the diastereoisomers.

The compounds used according to the instant disclosure therefore correspond to formula (I) or tautomer (I') below or their salts, their optical isomers, racemates, and/or solvates such as hydrates and the thereof, alone or as a mixture.

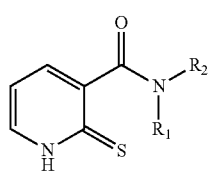

(I)

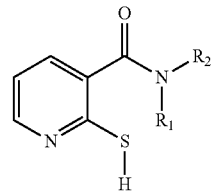

(I')

In which Formulas (I) and (I')
$R_1$ denotes a radical chosen from:
a) a hydrogen atom;
b) a saturated linear $C_1$-$C_{10}$ or branched $C_3$-$C_{10}$ alkyl group optionally substituted with one or more groups, which may be identical or different, chosen from:
i) —O—$R_3$
ii) —S—$R_3$;

$R_2$ denotes a radical chosen from:
a) a hydrogen atom;
b) a saturated hydrocarbonated group linear $C_1$-$C_{12}$ or branched $C_3$-$C_{12}$ or cyclic $C_3$-$C_8$, optionally substituted with one or more groups, which may be identical or different, chosen from:
i) —O—$R_3$
ii) —S—$R_3$
iii) —C(O) —O—$R_3$;
iv) a $C_5$-$C_{12}$ aryl group optionally substituted with one or more hydroxyls and/or with one or more $C_1$-$C_8$ alkoxy radicals;
c) a $C_5$-$C_{12}$ aryl group optionally substituted with one or more hydroxyls and/or with one or more $C_1$-$C_8$ alkoxy radicals $R_3$ denotes a radical chosen from:
a) a hydrogen atom;
b) a saturated linear $C_1$-$C_{10}$ or branched $C_3$-$C_{10}$ alkyl group;

The compound (I') is the tautomer form of the compound (I) when a tautomeric equilibrium exists according to the following scheme:

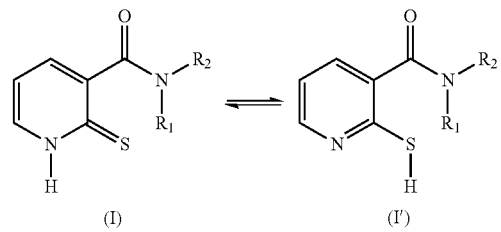

According to one embodiment of the disclosure $R_1$ represents one hydrogen atom.

According to another embodiment of the disclosure $R_1$ represents a linear ($C_1$-$C_{10}$)alkyl group or branched ($C_3$-$C_{10}$)alkyl group, especially a linear ($C_1$-$C_6$)alkyl group or branched ($C_3$-$C_6$)alkyl group, such as methyl, ethyl, n-pentyl, n-nonyl, isobutyl, more preferably ethyl. Particularly the said alkyl group of $R_1$ is not substituted.

According to one embodiment of the disclosure $R_2$ represents one hydrogen atom.

According to another embodiment of the disclosure $R_2$ represents a linear ($C_1$-$C_{10}$)alkyl group or branched ($C_3$-$C_{10}$)alkyl group, especially a linear ($C_1$-$C_6$)alkyl group or branched ($C_3$-$C_6$)alkyl group, such as methyl, ethyl, n-pentyl, n-nonyl, isobutyl, more preferably methyl or ethyl group; the said alkyl group of $R_2$ being not substituted.

According to another embodiment of the disclosure $R_2$ represents a linear ($C_1$-$C_{10}$)alkyl group or branched ($C_3$-$C_{10}$)alkyl group, especially a linear ($C_1$-$C_6$)alkyl group or branched ($C_3$-$C_6$)alkyl group, such as methyl, ethyl, n-pentyl, n-nonyl, isobutyl, more preferably methyl or ethyl; the said alkyl group being substituted by one or more groups selected from i), ii), iii) and iv) as defined herein before. Preferably the said alkyl group being substituted by one or two groups selected from i), ii) and iii), more preferably by one or two groups selected from i) and iii), better substituted by one group iii) as carboxy.

Another variant for radical $R_2$ is that the said alkyl group being substituted by one group iv) especially substituted by one phenyl group.

According to another embodiment of the disclosure $R_2$ represents a ($C_3$-$C_8$)cycloalkyl group, preferably a ($C_5$-$C_7$) cycloalkyl group such cyclohexyl.

According to another embodiment of the disclosure $R_2$ represents $C_5$-$C_{12}$ aryl group optionally substituted with one or more hydroxyls and/or with one or more $C_1$-$C_8$ alkoxy radicals, preferably a phenyl group particularly not substituted.

According to an embodiment $R_3$ represents a hydrogen atom.

According to another embodiment $R_3$ represents a saturated linear $C_1$-$C_{10}$ or branched $C_3$-$C_{10}$ alkyl group; particularly a linear ($C_1$-$C_6$)alkyl group or a branched ($C_3$-$C_6$)alkyl group, preferably ($C_1$-$C_4$)alkyl group such as methyl group.

Preferably, the compounds of formula (I) and tautomer (I') or their salts, their optical isomers, racemates, and/or solvates such as hydrates and the thereof, alone or as a mixture;
have the following meanings:
$R_1$ denotes a radical chosen from:
a) a hydrogen atom;
b) a saturated linear $C_1$-$C_6$ or branched $C_3$-$C_6$ alkyl group optionally substituted with one or more groups, which may be identical or different, chosen from:
i) —O—$R_3$
ii) —S—$R_3$;
preferably optionally substituted with one or more groups i)
$R_2$ denotes a radical chosen from:
a) a hydrogen atom;
b) a saturated hydrocarbonated group linear $C_1$-$C_{10}$ or branched $C_3$-$C_{10}$ or cyclic $C_3$-$C_8$ such as C5-C6, optionally substituted with one or more groups, which may be identical or different, chosen from:
i) —O—$R_3$
ii) —SR-$_3$
iii) —C(O) —O—$R_3$;
iv) a phenyl group optionally substituted with one or more hydroxyls and/or with one or more $C_1$-$C_4$ alkoxy radicals such as methoxy;
preferably substituted with one or more groups selected from i) and iii), preferably iii) such as carboxy
$R_3$ denotes a radical chosen from:
a) a hydrogen atom;
b) a saturated linear $C_1$-$C_6$ or branched $C_3$-$C_6$ alkyl group Preferentially, the compounds of formula (I) and tautomer (I') or their salts, their optical isomers, racemates, and/or solvates such as hydrates and the thereof, alone or as a mixture;
have the following meanings:
$R_1$ denotes a radical chosen from:
a) a hydrogen atom;
b) a saturated linear $C_1$-$C_4$ or branched $C_3$-$C_4$ alkyl group optionally substituted with one or more groups, which may be identical or different, chosen from i) —O$R_3$, more preferably not substituted;
$R_2$ denotes a radical chosen from:
a) a hydrogen atom;
b) a saturated hydrocarbonated group linear $C_1$-$C_{10}$ or branched $C_3$-$C_{10}$ or cyclic $C_3$-$C_8$ as C5-C6, optionally substituted with one or more groups, which may be identical or different, chosen from:
i) —O—$R_3$
iii) —C(O) —O—$R_3$;
iv) a $C_5$-$C_{12}$ aryl group optionally substituted with one or more hydroxyls and/or with one or more $C_1$-$C_4$ alkoxy radicals;
$R_3$ denotes a radical chosen from:
a) a hydrogen atom;
b) a saturated linear $C_1$-$C_4$ or branched $C_3$-$C_4$ alkyl group such as methyl or ethyl.

Preferentially, the compounds of formula (I) and tautomer (I') or their salts, their optical isomers, racemates, and/or solvates such as hydrates and the thereof, alone or as a mixture;
have the following meanings:
$R_1$ is a hydrogen atom; and
$R_2$ denotes a radical chosen from:
a) a hydrogen atom;
b) a saturated hydrocarbonated group linear $C_1$-$C_5$ or branched $C_3$-$C_5$ or cyclic $C_3$-$C_8$ as C5-C6, substituted with one or more groups, which may be identical or different, chosen from v) —C(O) —O—$R_3$, preferably substituted with one group iii) —C(O) —O—$R_3$;
$R_2$ is even more preferably a saturated hydrocarbonated group linear $C_1$-$C_4$ or branched $C_3$-$C_4$ substituted with one group iii) —C(O) —O$R_3$.

According to another preferred embodiment, compounds of formula (I) and tautomer (I') are selected among compounds of formula (II) and also the tautomers thereof, the salts thereof, the solvates thereof and the optical isomers thereof, and the racemates thereof, alone or as a mixture:

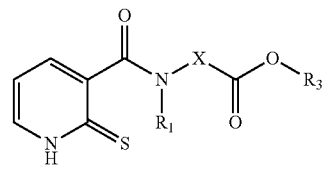

(II)

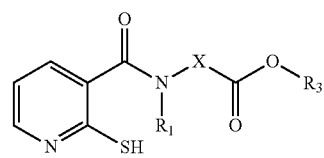

(II')

Formula (I) and (I') Wherein $R_1$ and $R_3$ have the same meaning than for compounds of formula (I) and (I') and X denotes an alkylene radical —$(CH_2)_n$— with n being an integer ranging inclusively from 1 to 10, preferably ranging from i to 6, more preferably ranging from 1 to 4, such as 1, preferably $R_3$ represents a hydrogen atom.

Among the compounds of formula (I), the following compounds are preferably used and their tautomer or their salts, their optical isomers, racemates, and/or solvates such as hydrates and the thereof, alone or as a mixture:

| No. | Structure | Chemical name | CAS No. |
|---|---|---|---|
| 1 | 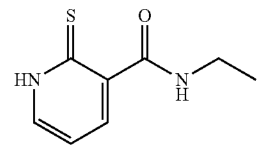 | N-ethyl-2-thioxo-1,2-dihydropyridine-3-carboxamide | 91859-75-5 |
| 2 | 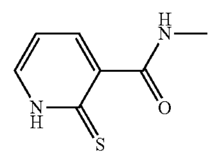 | N-methyl-2-thioxo-1,2-dihydropyridine-3-carboxamide | 91859-74-4 |
| 3 | 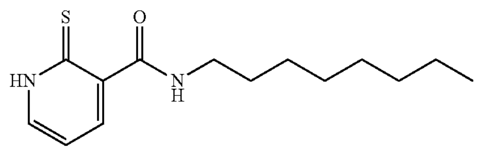 [SMILES: CCCCCCCCNC(=O)c1ccc[nH]c1=S] | N-octyl-2-thioxo-1,2-dihydropyridine-3-carboxamide | 91859-77-7 |
| 4 | 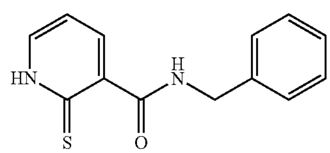 [SMILES: O=C(NCc1ccccc1)c1ccc[nH]c1=S] | N-benzyl-2-thioxo-1,2-dihydropyridine-3-carboxamide | 91859-79-9 |
| 5 | 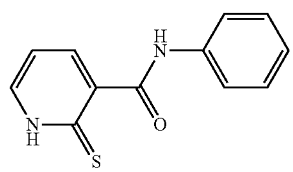 [SMILES: O=C(Nc1ccccc1)c1ccc[nH]c1=S] | N-phenyl-2-thioxo-1,2-dihydropyridine-3-carboxamide | 104857-16-1 |
| 6 | 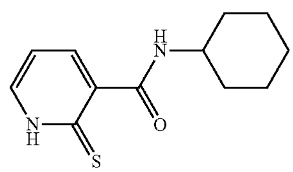 [SMILES: O=C(NC1CCCCC1)c1ccc[nH]c1=S] | N-cyclohexyl-2-thioxo-1,2-dihydropyridine-3-carboxamide | 91859-78-8 |
| 7 | 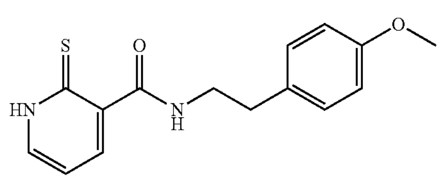 [SMILES: COc1ccc(CCNC(=O)c2ccc[nH]c2=S)cc1] | N-[2-(4-methoxyphenyl)ethyl]-2-thioxo-1,2-dihydropyridine-3-carboxamide | 923682-88-6 |
| 8 | 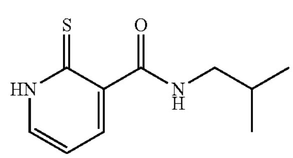 | N-(2-methylpropyl)-2-thioxo-1,2-dihydropyridine-3-carboxamide | 1100027-79-9 |
| 9 | 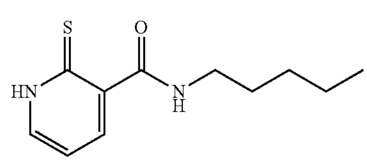 | N-pentyl-2-thioxo-1,2-dihydropyridine-3-carboxamide | 330667-57-7 |

| No. | Structure | Chemical name | CAS No. |
|---|---|---|---|
| 10 | 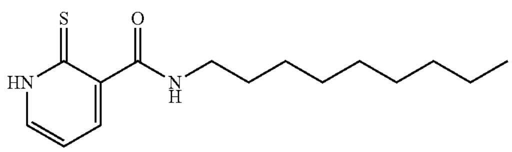 [SMILES: CCCCCCCCCNC(=O)c1ccc[nH]c1=S] | N-nonyl-2-thioxo-1,2-dihydropyridine-3-carboxamide | 1031149-44-6 |
| 11 | 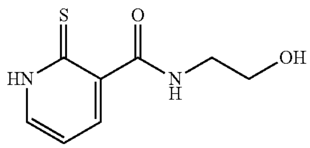 [SMILES: O=C(NCCO)c1ccc[nH]c1=S] | N-(2-hydroxyethyl)-2-thioxo-1,2-dihydropyridine-3-carboxamide | |
| 12 | 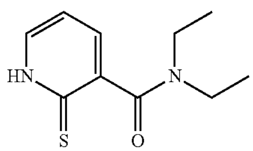 | N,N-diethyl 2-mercaptonicotinamide | |
| 13 | 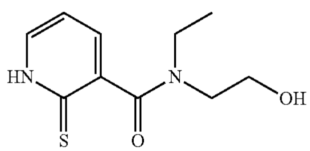 | N-ethyl-N-(2-hydroxyethyl)-2-thioxo-1,2-dihydropyridine-3-carboxamide | |
| 14 | 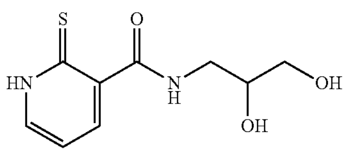 [SMILES: O=C(NCC(O)CO)c1ccc[nH]c1=S] | N-(2,3-dihydroxypropyl)-2-thioxo-1,2-dihydropyridine-3-carboxamide | |
| 15 | 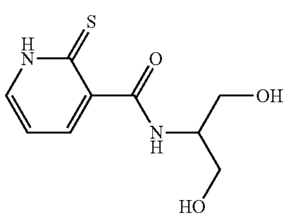 [SMILES: O=C(NC(CO)CO)c1ccc[nH]c1=S] | N-(1,3-dihydroxypropan-2-yl)-2-thioxo-1,2-dihydropyridine-3-carboxamide | |
| 16 | 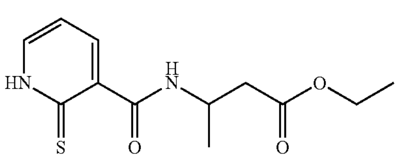 [SMILES: CCOC(=O)CC(C)NC(=O)c1ccc[nH]c1=S] | Ethyl N-[(2-thioxo-1,2-dihydropyridin-3-yl)carbonyl]alaninate | |
| 17 | 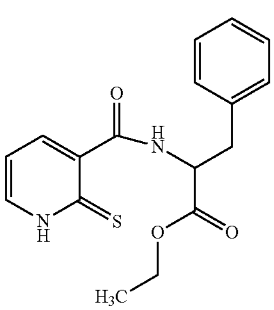 [SMILES: CCOC(=O)C(Cc1ccccc1)NC(=O)c1ccc[nH]c1=S] | Ethyl N-[(2-thioxo-1,2-dihydropyridin-3-yl)carbonyl]phenylalaninate | |

-continued

| No. | Structure | Chemical name | CAS No. |
|---|---|---|---|
| 18 | 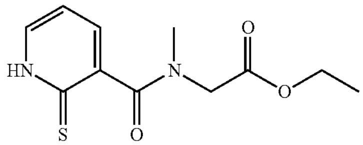 | Ethyl N-methyl-N-[(2-thioxo-1,2-dihydropyridin-3-yl)carbonyl]glycinate | |
| 19 | 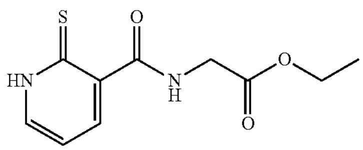 [SMILES: CCOC(=O)CNC(=O)c1ccc[nH]c1=S] | Ethyl N-[(2-thioxo-1,2-dihydropyridin-3-yl)carbonyl]glycinate | |
| 20 | 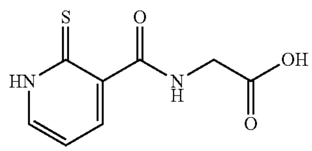 | N-[(2-thioxo-1,2-dihydropyridin-3-yl)carbonyl]glycine | |
| 21 | 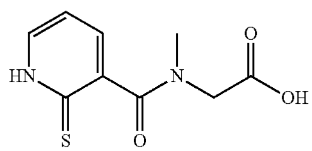 | N-methyl-N-[(2-thioxo-1,2-dihydropyridin-3-yl)carbonyl]glycine | |
| 22 | 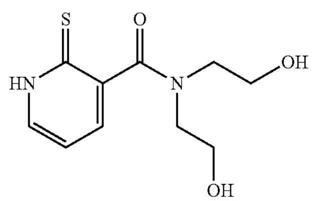 [SMILES: O=C(c1ccc[nH]c1=S)N(CCO)CCO] | N,N-bis(2-hydroxyethyl)-2-thioxo-1,2-dihydropyridine-3-carboxamide | |
| 23 | 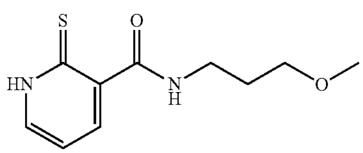 | N-(3-methoxypropyl)-2-thioxo-1,2-dihydropyridine-3-carboxamide | |
| 24 | 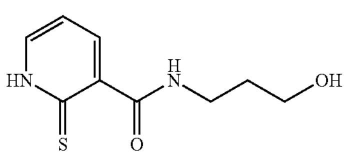 [SMILES: O=C(NCCCO)c1ccc[nH]c1=S] | N-butyl-2-thioxo-1,2-dihydropyridine-3-carboxamide | |

Among these compounds, the following compounds are more particularly preferred:

| No. | Structure | Chemical name | CAS No. |
|---|---|---|---|
| 1 | 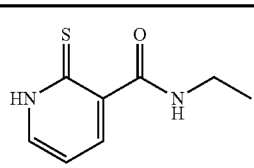 | N-ethyl-2-thioxo-1,2-dihydropyridine-3-carboxamide | 91859-75-5 |

-continued

| No. | Structure | Chemical name | CAS No. |
|---|---|---|---|
| 2 | 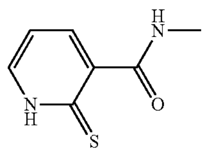 | N-methyl-2-thioxo-1,2-dihydropyridine-3-carboxamide | 91859-74-4 |
| 4 | 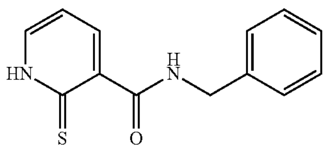 [SMILES: O=C(NCc1ccccc1)c1ccc[nH]c1=S] | N-benzyl-2-thioxo-1,2-dihydropyridine-3-carboxamide | 91859-79-9 |
| 6 | 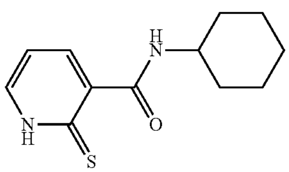 [SMILES: O=C(NC1CCCCC1)c1ccc[nH]c1=S] | N-cyclohexyl-2-thioxo-1,2-dihydropyridine-3-carboxamide | 91859-78-8 |
| 7 | 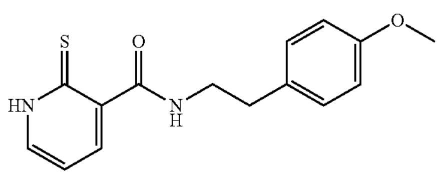 [SMILES: COc1ccc(CCNC(=O)c2ccc[nH]c2=S)cc1] | N-[2-(4-methoxyphenyl)ethyl]-2-thioxo-1,2-dihydropyridine-3-carboxamide | 923682-88-6 |
| 9 | 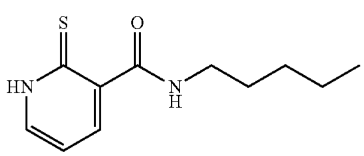 | N-pentyl-2-thioxo-1,2-dihydropyridine-3-carboxamide | 330667-57-7 |
| 11 | 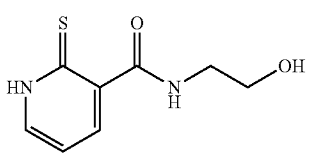 [SMILES: O=C(NCCO)c1ccc[nH]c1=S] | N-(2-hydroxyethyl)-2-thioxo-1,2-dihydropyridine-3-carboxamide | |
| 12 | 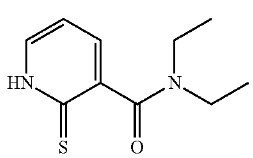 | N,N-diethyl 2-mercaptonicotinamide | |
| 14 | 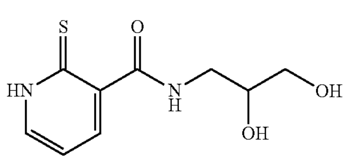 [SMILES: O=C(NCC(O)CO)c1ccc[nH]c1=S] | N-(2,3-dihydroxypropyl)-2-thioxo-1,2-dihydropyridine-3-carboxamide | |
| 15 | 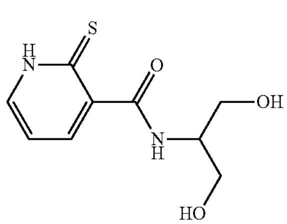 [SMILES: O=C(NC(CO)CO)c1ccc[nH]c1=S] | N-(1,3-dihydroxypropan-2-yl)-2-thioxo-1,2-dihydropyridine-3-carboxamide | |

| No. | Structure | Chemical name | CAS No. |
|---|---|---|---|
| 16 | 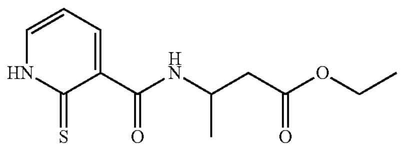 [SMILES: CCOC(=O)CC(C)NC(=O)c1ccc[nH]c1=S] | Ethyl N-[(2-thioxo-1,2-dihydropyridin-3-yl)carbonyl]alaninate | |
| 17 | 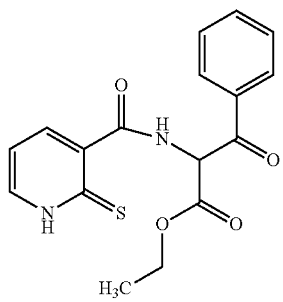 [SMILES: CCOC(=O)C(NC(=O)c1ccc[nH]c1=S)C(=O)c1ccccc1] | Ethyl N-[(2-thioxo-1,2-dihydropyridin-3-yl)carbonyl]phenyl alaninate | |
| 18 | 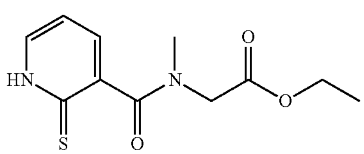 [SMILES: CCOC(=O)CN(C)C(=O)c1ccc[nH]c1=S] | Ethyl N-methyl-N-[(2-thioxo-1,2-dihydropyridin-3-yl)carbonyl]glycinate | |
| 19 | 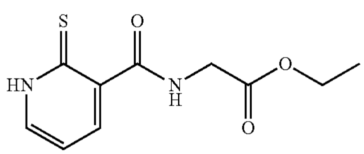 [SMILES: CCOC(=O)CNC(=O)c1ccc[nH]c1=S] | Ethyl N-[(2-thioxo-1,2-dihydropyridin-3-yl)carbonyl]glycinate | |
| 20 | 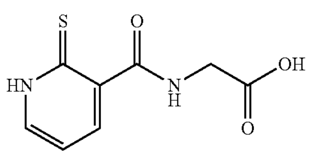 [SMILES: O=C(O)CNC(=O)c1ccc[nH]c1=S] | N-[(2-thioxo-1,2-dihydropyridin-3-yl)carbonyl]glycine | |
| 21 | 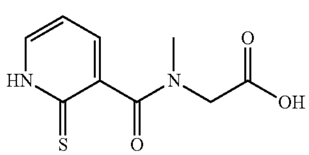 | N-methyl-N-[(2-thioxo-1,2-dihydropyridin-3-yl)carbonyl]glycine | |

More preferably, among these compounds, the following compounds are more particularly preferred:

| No. | Structure | Chemical name | CAS No. |
|---|---|---|---|
| 1 | 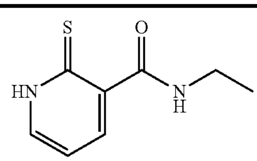 | N-ethyl-2-thioxo-1,2-dihydropyridine-3-carboxamide | 91859-75-5 |
| 9 | 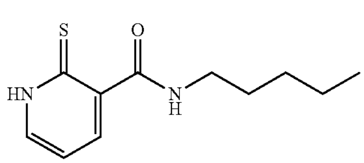 | N-pentyl-2-thioxo-1,2-dihydropyridine-3-carboxamide | 330667-57-7 |

-continued

| No. | Structure | Chemical name | CAS No. |
|---|---|---|---|
| 16 | 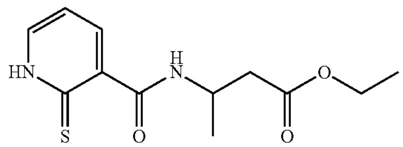 [SMILES: CCOC(=O)CC(C)NC(=O)c1ccc[nH]c1=S] | Ethyl N-[(2-thioxo-1,2-dihydropyridin-3-yl)carbonyl]alaninate | |
| 18 | 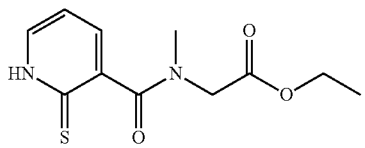 [SMILES: CCOC(=O)CN(C)C(=O)c1ccc[nH]c1=S] | Ethyl N-methyl-N-[(2-thioxo-1,2-dihydropyridin-3-yl)carbonyl]glycinate | |
| 19 | 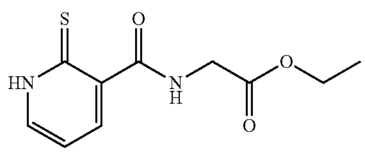 [SMILES: CCOC(=O)CNC(=O)c1ccc[nH]c1=S] | Ethyl N-[(2-thioxo-1,2-dihydropyridin-3-yl)carbonyl]glycinate | |
| 20 | 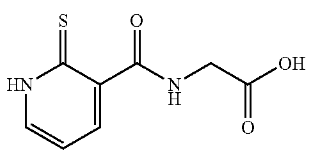 [SMILES: O=C(O)CNC(=O)c1ccc[nH]c1=S] | N-[(2-thioxo-1,2-dihydropyridin-3-yl)carbonyl]glycine | |
| 21 | 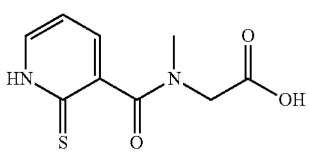 | N-methyl-N-[(2-thioxo-1,2-dihydropyridin-3-yl)carbonyl]glycine | |

Even more preferably, among these compounds, the following compounds are more particularly preferred:

| No. | Structure | Chemical name | CAS No. |
|---|---|---|---|
| 18 | 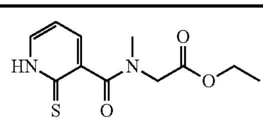 | Ethyl N-methyl-N-[(2-thioxo-1,2-dihydropyridin-3-yl)carbonyl]glycinate | |
| 19 | 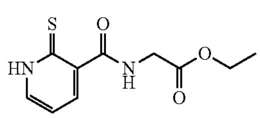 [SMILES: CCOC(=O)CNC(=O)c1ccc[nH]c1=S] | Ethyl N-[(2-thioxo-1,2-dihydropyridin-3-yl)carbonyl]glycinate | |
| 20 | 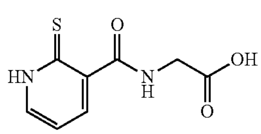 [SMILES: O=C(O)CNC(=O)c1ccc[nH]c1=S] | N-[(2-thioxo-1,2-dihydropyridin-3-yl)carbonyl]glycine | |
| 21 | 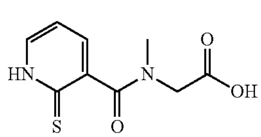 | N-methyl-N-[(2-thioxo-1,2-dihydropyridin-3-yl)carbonyl]glycine | |

In a most preferred embodiment, the compound according to the instant disclosure is the following:

| No. | Structure | Chemical name |
|---|---|---|
| 20 | 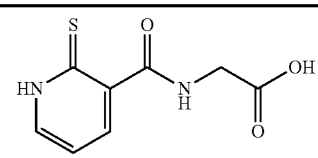 | N-[(2-thioxo-1,2-dihydropyridin-3-yl)carbonyl]glycine |

All compounds can be obtained by chemical method known by man skilled in the art, from commercially available reagents. We can for example use the synthetic method disclosed in the European patent application EP3 390 363.

The composition used according to the disclosure comprises at least one compound of formulae (I) and/or (II) as described above, in a physiologically acceptable medium.

The compound (1), (I'), (II) and/or (II') may be present in the composition used according to the disclosure in an amount which may be between 0.01% and 10% by weight, preferably between 0.1% and 5% by weight, in particular from 0.5% to 3% by weight, relative to the total weight of the composition.

Natural Emulsifiers

In various embodiments, the natural emulsifiers may be chosen from: Inulin Lauryl Carbamate, $C_{12}$-20 Alkyl Glucoside, Cetearyl Alcohol (and) Cetearyl Glucoside, APGs, Arachidyl Alcohol (And) Behenyl Alcohol (And) Arachidyl Glucoside, Polyglyceryl-3 Methylglucose Distearate, Cetearyl wheat straw glycosides and Cetearyl alcohol, Sorbitan Olivate, Glyceryl citrate stearate, Cetearyl Olivate (and) Sorbitan Olivate, other sucrose and glucose esters and ethers, amino acid-based emulsifiers, Hydrogenated lecithin, lecithins, Sodium lauroyl glutamate, sodium stearoyl glutamate and a mixture thereof.

Suitable hydrophobically-modified natural emulsifiers include, for example, inulin lauryl carbamate, commercially available from Beneo Orafti under the tradename Inutec Sp1.

Suitable natural emulsifiers with an HLB around about 10 include, but are not limited to, polyglycerides and mixture thereof.

The fatty acid esters of a sugar that can be used as nonionic amphiphilic lipids can be chosen in particular from the group comprising esters or mixtures of esters of a C8-C22 fatty acid and of sucrose, of maltose, of glucose or of fructose, and esters or mixtures of esters of a C14-C22 fatty acid and of methylglucose. The C8-C22 or C14-C22 fatty acids forming the fatty unit of the esters that can be used in the emulsion comprise a saturated or unsaturated linear alkyl chain having, respectively, from 8 to 22 or from 14 to 22 carbon atoms. The fatty unit of the esters can be chosen in particular from stearates, behenates, arachidonates, palmitates, myristates, laurates, caprates and mixtures thereof.

By way of example of esters or of mixtures of esters of a fatty acid and of sucrose, of maltose, of glucose or of fructose, mention may be made of sucrose monostearte, sucrose distearate, sucrose tristearate and mixtures thereof, such as the products sold by the company Croda under the name Crodesta F50, F70, F1 10 and F160 having, respectively, an HLB (Hydrophilic Lipophilic Balance) of 5, 7, 1 1 and 16; and, by way of example of esters or of mixtures of esters of a fatty acid and of methylglucose, mention may be made of the disearate of methylglucose and of polyglycerol-3, sold by the company Goldschmidt under the name Tego-care 450. Mention may also be made of glucose monoesters or maltose monoesters, such as methyl 0-hexadecanoyl-6-D-glucoside and O-hexadecanoyl-6-D-maltoside.

The fatty alcohol ethers of a sugar that can be used as nonionic amphiphilic lipids can be chosen in particular form the group comprising ethers or mixtures of ethers of a C8-C22 fatty alcohol and of glucose, of maltose, of sucrose or of fructose, and ethers or mixtures of ethers of a C 4-C22 fatty alcohol and of methylglucose. They are in particular alkylpolyglucosides.

The C8-C22 or C14-C22 fatty alcohols forming the fatty unit of the ethers that can be used in the emulsion of the instant disclosure comprise a saturated or unsaturated linear alkyl chain having, respectively, from 8 to 22 or from 14 to 22 carbon atoms. The fatty unit of the ethers can be chosen in particular from decyl, cetyl, behenyl, arachidyl, stearyl, palmityl, myristyl, lauryl, capryl and hexadecanoyl units, and mixtures thereof such as cetearyl.

By way of example of fatty alcohol ethers of a sugar, mention may be made of alkylpolyglucosides, such as decylglucoside and laurylglucoside sold, for example, by the company Henkel under the respective names Plantaren 2000 and Plantaren 1200, cetosetarylglucoside, optionally as a mixture with cetostearyl alcohol, sold, for example, under the name Montanov 68 by the company Seppic, under the name Tego-care CG90 by the company.

Goldschmidt and under the name Emulgade KE3302 by the company Henkel, and also arachidylglucoside, for example in the form of the mixture of arachidyl and behenyl alcohols and of arachidylglucoside sold under the name Montanov 202 by the company Seppic.

Use is more particularly made, as nonionic amphiphilic lipid of this type, of sucrose monostearate, sucrose distearate, sucrose tristearate and mixtures thereof, the distearate of methylglucose and of polyglycerol-3, and alkylpolyglucosides.

The natural emulsifiers having an HLB from around about 10 to about 15 will typically be employed in an amount of from about 0.5 to about 8 wt. %, based on the total weight of the composition.

The total amount of natural emulsifier present in the compositions is typically in an amount of about 0.5, 0.6, 0.7, 0.8, 0.9, 1.0, 1.2, 1.4, 1.6, 1.8, 2.0, 2.2, 2.4, 2.6, 2.8, 3.0 wt % to about 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.5 or 8.0 wt. %, based on the total weight of the composition.

pH Adjusting Agent

The composition according to the present invention may comprise at least one pH adjusting agent (pH adjuster). Two or more pH adjusting agents may be used in combination. Thus, a single type of pH adjusting agent or a combination of different types of pH adjusting agents may be used.

As the pH adjusting agent, at least one acidifying agent and/or at least one basifying agent (alkaline agent) may be used.

The acidifying agent may be a monovalent or polyvalent, such as divalent, acid.

The acidifying agents can be, for example, mineral (inorganic) acids such as hydrochloric acid, sulfuric acid, phosphoric acid, or organic acids such as carboxylic acids, for instance tartaric acid, citric acid, and lactic acid, as well as sulphonic acids.

The basifying agent may be a monovalent or polyvalent, such as divalent, base.

The basifying agents may be mineral (inorganic) or organic, or hybrid.

The mineral basifying agents may be chosen from aqueous ammonia; alkali metal carbonates or bicarbonates such as sodium or potassium carbonates and sodium or potassium bicarbonates; alkali metal hydroxides such as sodium hydroxide and potassium hydroxide; and mixtures thereof.

The organic basifying agents may be chosen from organic amines with a pKb at 25° C. of less than 12, preferably less than 10, and even more advantageously less than 6. It should be noted that it is the pKb corresponding to the function of highest basicity. In addition, the organic amines do not comprise any alkyl or alkenyl fatty chains comprising more than ten carbon atoms.

The organic basifying agent may be chosen, for example, from alkanolamines, oxyethylenated and/or oxypropylenated ethylenediamines, amino acids and amine compounds of formula (III) below:

(III)

in which

W represents a $C_1$-$C_6$ divalent alkylene radical optionally substituted with one or more hydroxyl groups or a $C_1$-$C_6$ alkyl radical, and optionally interrupted with one or more heteroatoms such as O and N, and $R_x$, $R_y$, $R_z$, and $R_t$, which may be identical or different, represent a hydrogen atom or a $C_1$-$C_6$ alkyl, $C_1$-$C_6$ hydroxyalkyl, or $C_1$-$C_6$ aminoalkyl radical.

Examples of the amine compounds of formula (III) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Alkanolamines such as monoalkanolamines, dialkanolamines or trialkanolamines comprising one to three identical or different $C_1$-$C_4$ hydroxyalkyl radicals may be suitable for the present invention. Among the compounds of this type, mention may be made of monoethanolamine (MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

Amino acids that may be used are of natural or synthetic origin, in their L, D or racemic form, and comprise at least one acid function chosen more particularly from carboxylic acid, sulfonic acid, phosphonic acid or phosphoric acid functions. The amino acids may be in neutral or ionic form.

As amino acids that may be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

It may be preferable that the amino acids are basic amino acids comprising an additional amine function optionally included in a ring or in an ureido function.

Such basic amino acids may preferably be chosen from those corresponding to formula (IV) below:

(IV)

in which
R represents a group chosen from:

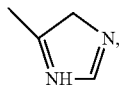

(CH$_2$)$_3$-NH2,
(CH$_2$)$_2$-NH2,
(CH$_2$)$_2$-NH—CO—NH2, and

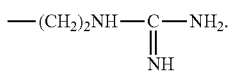

The compounds corresponding to formula (IV) include histidine, lysine, arginine, ornithine and citrulline.

The organic basifying agent may be chosen from organic amines of heterocyclic type. Besides histidine that has already been mentioned in the amino acids, mention may in particular be made of pyridine, piperidine, imidazole, triazole, tetrazole and benzimidazole.

The organic basifying agent may also be chosen from amino acid dipeptides. As amino acid dipeptides that may be used in the present invention, mention may be made especially of carnosine, anserine and baleine.

The organic basifying agent may also be chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethyl-guanidine, glycocyamine, metformin, agmatine, N-amidinoalanine, 3-guanidino-propionic acid, 4-guanidinobutyric acid and 2-([amino(imino)methyl]amino)ethane-1-sulfonic acid.

In a preferred embodiment of the present invention, the organic basifying agent may be selected from amino acids, preferably basic amino acids, and more preferably arginine, lysine, histidine or mixtures thereof. Even more preferentially, the organic basifying agent may be arginine.

Hybrid compounds that may be mentioned include the salts of the amines mentioned previously with acids such as carbonic acid or hydrochloric acid. Guanidine carbonate or monoethanolamine hydrochloride may be used in particular.

The pH adjusting agent may be present in an amount of 0.01% by weight or more, preferably 0.05% by weight or more, and more preferably 0.1% by weight or more, relative to the total weight of the composition.

The pH adjusting agent may be present in an amount of 15% by weight or less, preferably 10% by weight or less, and more preferably 5% by weight or less, relative to the total weight of the composition.

The pH adjusting agent may be present in an amount ranging from 0.01% to 15% by weight, preferably from 0.05% to 10% by weight, and more preferably from 0.1% to 5% by weight or less, relative to the total weight of the composition.

It is preferable that the composition according to the present invention have a pH of 4.5 or more, and more preferably 5 or more.

It is preferable that the composition according to the present invention have a pH of 6.5 or less, and more preferably 6 or less.

It is preferable that the composition according to the present invention have a pH of from 4.5 to 6.5, and more preferably from 5 to 6.

The pH of the composition means the pH of the aqueous phase of the composition according to the present invention.

It may be preferable that at least one buffer or buffering agent also be used, as the pH adjusting agent, in combination with the acidifying agent and/or the basifying agent, in order to stabilize the pH of the composition according to the present invention.

As the buffer, any of commonly known buffers may be used. For example, salts of acids or bases, preferably salts of weak acids or weak bases, may be used. For example, sodium citrate or sodium lactate may be used as the buffer, if citric acid or lactic acid is used as the acidifying agent.

Cosmetically Acceptable Carrier System

The cosmetic compositions include a cosmetically acceptable carrier system. The term "cosmetically acceptable" means a carrier that is compatible with any keratinous substrate, and for purposes hereof, includes water and optionally water based solvents subject to any exclusions as disclosed herein.

The cosmetic compositions may comprise any constituent normally employed in the topical application and administration envisaged. Mention may in particular be made of water, solvents, fatty compounds (i.e. described by the International Federation Societies of Cosmetic Chemists, for example, in Cosmetic Raw Material Analysis and Quality, Volume I: Hydrocarbons, Glycerides, Waxes and Other Esters (Redwood Books, 1994), which is incorporated herein by reference in its entirety), polyols, pigments, fillers, silicones, surfactants, thickeners, gelling agents, preservatives and their mixtures in all proportions.

Methods of Use

The instant disclosure also relates to methods of using the cosmetic compositions described herein. For example, the cosmetic compositions can be used in a method that comprises applying the cosmetic compositions to the skin of humans. In some cases, the composition is applied to the face. Furthermore, the cosmetic composition can be used in methods for depigmenting and/or bleaching keratin materials, preferably skin, comprising the step of: applying to the keratin substance the composition according to the compositions described herein. The aforementioned methods are non-therapeutic.

The instant disclosure also relates to non-therapeutic cosmetic process for depigmenting, lightening and/or bleaching keratin materials, preferably skin, comprising the step of applying to the keratin substance the composition according to the compositions described herein.

The cosmetic composition may be applied once per day, twice per day, or more than once or twice per day. In some cases, the composition is applied in the evenings before bed. In other cases, the compositions are applied in the morning. In still other cases, the composition may be applied immediately after washing the skin. The compositions may be used once, or for a series of days, weeks, or months. For example, the compositions may be used daily for a period of 1, 2, 3, 4, 5, 6, 7, 8 or more weeks, or months.

EXAMPLES

Implementation of the present disclosure is provided by way of the following examples. The following examples serve to elucidate aspects of the technology without being limiting in nature.

Example 1

Example 1: Synthesis of Compound 20

Compound 20 is synthesized as disclosed in example 2 of patent EP3 390 363.

Example 2

Inventive Compositions

The inventive compositions were prepared using the following general procedure:

Generally, the water soluble raw materials (minus actives) were added to the main kettle and dissolved. Polymers were then added and mixed until well-dispersed. Batch was heated to 75 C. In a side kettle, the fatty compounds, silicones, and emulsifiers/surfactants were mixed together and heated to 75 C. The side kettle was added to the main kettle while homogenizing well. When well emulsified, the batch was cooled to room temperature, and actives and fillers were added.

TABLE 1

Inventive Compositions

| | | Inventive Ex. 1 | Inventive Ex. 2 |
|---|---|---|---|
| | Compound of Thiopyridinone type (THP) | 0.50 | 0.50 |
| Natural Emulsifier | Inulin Lauryl Carbamate | | |
| | Polyglyceryl-3 Methylglucose Distearate | | 0.50 |
| | C14-22 Alcohols (And) C12-20 Alkyl Glucoside | 1.50 | |
| | Hydrogenated Lecithin | 0.30 | 0.30 |
| | Cetearyl Alcohol (And) Cetearyl Glucoside Glyceryl Stearate | 0.50 | 1.00 |
| | Polyglyceryl-4 Caprate | | 1.50 |
| Non Natural Emulsifers | Peg-40 Stearate | | |
| | Peg-20 Methyl Glucose Sesquistearate | | |
| | Poloxamer 338 | | |
| Fatty Compound | Fatty Compound | 6.00 | 9.00 |
| Filler | Filler | 0.15 | 1.15 |
| Polymer | Polymer | 0.70 | 0.65 |
| Preservative | Preservative | 0.80 | 0.60 |
| Silicon | Silicon | 2.00 | 0.00 |
| Polyols | Polyols | 12.00 | 9.00 |
| Active Agent | Active Agent | 5.25 | 5.25 |
| Adjuvant | Adjuvant | 1.76 | 1.70 |
| Water | Water | Q.S. | Q.S. |

TABLE 2

Comparative Compositions

| | | Comparative Ex. 1 | Comparative Ex. 2 |
|---|---|---|---|
| Active Compound | Compound of Thiopyridinone type (THP) | 0.50 | 0.50 |
| Natural Emulsifier | Inulin Lauryl Carbamate | | 4.00 |
| | Polyglyceryl-3 Methylglucose Distearate | | |
| | C14-22 Alcohols (And) C12-20 Alkyl Glucoside | | 1.50 |
| | Hydrogenated Lecithin | | 0.30 |
| | Cetearyl Alcohol (And) Cetearyl Glucoside Glyceryl Stearate | | |
| | Polyglyceryl-4 Caprate | 1.80 | |
| Non Natural Emulsifers | Peg-40 Stearate | | |
| | Peg-20 Methyl Glucose Sesquistearate | 2.00 | |
| | Poloxamer 338 | 0.60 | |
| Fatty Compound | Fatty Compound | 3.00 | 4.90 |
| Filler | Filler | 0.40 | 0.80 |
| Polymer | Polymer | 1.60 | 1.90 |
| Preservative | Preservative | 0.60 | 0.80 |
| Silicon | Silicon | 3.00 | 2.00 |
| Polyols | Polyols | 4.00 | 4.00 |
| Active Agent | Active Agent | 10.25 | 5.25 |
| Adjuvant | Adjuvant | 1.58 | 3.07 |
| Water | Water | Q.S. | Q.S. |

Example 3

Inventive Examples and Comparative Examples were tested for stability. The stability of the inventive and comparative Examples was assessed by following the procedure described below.

24 hours after processing, formulas were visually and sensorially assessed for homogeneity (e.g., no visible separation of phases, syneresis, texture was homogenous as opposed to contain solid parts.) Then, samples were placed in glass jars and placed in temperature controlled chambers at 25° C. and 45° C. After 2 weeks, samples were again checked for the aforementioned homogeneity. Acceptable results meant initial stability was acceptable. Acceptable samples were kept in chamber for further analysis over time.

The results are shown in Table 3 below.

TABLE 3

Stability Results with Inventive and Comparative Composition

| | Natural emulsifiers used | Non-natural emulsifiers used | Result | Comments |
| --- | --- | --- | --- | --- |
| Comparative Ex. 1 | | Peg-20 Methyl Glucose Sesquistearate Poloxamer 338 | Acceptable initial stability[1] | expected stability with a non-natural emulsifiers |
| Comparative Ex. 2 | Inulin Lauryl Carbamate | Potassium Cetyl Phosphate | Poor initial stability[2] | if mixed natural emulsifiers with natural emulsifier, composition is not stable so mixing both does not mean that it is obvious to work |
| Inventive Ex. 1 | C12-20 Alkyl Glucoside Inulin Lauryl Carbamate Hydrogenated Lecitihin | N/A | Acceptable initial stability | unexpected results. Compositions is stable without non-natural emulsifiers |
| Inventive Ex. 2 | Polyglyceryl-3 Methylglucose Distearate C12-20 Alkyl Glucoside Hydrogenated Lecitihin | N/A | Acceptable initial stability | unexpected results. Compositions is stable without non-natural emulsifiers |

[1]= means the emulsion is stable and homogenous during and soon after processing, and is also stable after at least 2 months at 25° C. and 45° C.
[2]= could be anything from product being not homogenous in texture to after formulation to noticeable separation of phases after 2 weeks at 25° C. and/or 45° C.

The results demonstrated that it is possible to formulate stable, direct emulsions containing THP, using natural emulsifiers, rather than PEG-containing emulsifiers, which are mainly synthetic emulsifiers. Indeed, THP could be included into a physically stable high viscosity emulsion containing more than 15% of fatty acids. However, having a slightly lower viscosity emulsion would allow for many more architectures with vastly different sensorial attributes. Thinner creams, lotions, and serums containing THP could be developed with natural emulsifiers, while remaining stable and sensorial.

While the disclosure has been described with reference to described embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The term "INCI" is an abbreviation of International Nomenclature of Cosmetic Ingredients, which is a system of names provided by the International Nomenclature Committee of the Personal Care Products Council to describe personal care ingredients.

The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is.

"At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" indicates that no reliably measurable excluded material is present in the composition, typically 0% by weight, based on the total weight of the composition. The term "essentially free" means that, while it prefers that no excluded material is present in the composition, it is possible to have very small amounts of the excluded material in the composition of the disclosure, provided that these amounts do not materially affect the advantageous properties of the composition. In particular, "essentially free" means that excluded material can be present in the composition at an amount of less than about 0.1% by weight, based on the total weight of the composition.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

The terms "weight percent" and "wt %" may be used interchangeably and mean percent by weight, based on the total weight of a composition, article or material, except as may be specified with respect to, for example, a phase, or a system that is a component of a composition, article or material. All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. An oil-in-water cosmetic composition comprising:
i) at least one compound selected from a compound of formula (I) and a tautomer of formula (I') their salts; their optical isomers, racemates, solvates, or a mixture thereof:

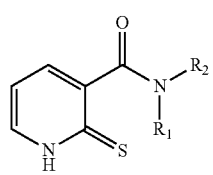
(I)

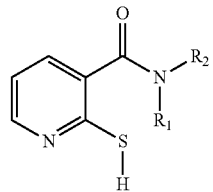
(I')

wherein Formulas (I) and (I'):
$R_1$ denotes a radical chosen from:
a) a hydrogen atom; or
b) a saturated linear $C_1$-$C_{10}$ or branched $C_3$-$C_{10}$ alkyl group optionally substituted with one or more groups, which may be identical or different, chosen from:
i) —O—$R_3$; or
ii) —S—$R_3$;
$R_2$ denotes a radical chosen from:
a) a hydrogen atom;
b) a saturated hydrocarbonated group linear $C_1$-$C_{12}$ or branched $C_3$-$C_{12}$ or cyclic $C_3$-$C_8$, optionally substituted with one or more groups, which may be identical or different, chosen from:
i) —O—$R_3$
ii) —S—$R_3$; or
iii) —C(O)—O—$R_3$;
iv) a $C_5$-$C_{12}$ aryl group optionally substituted with one or more hydroxyls and/or with one or more $C_1$-$C_5$ alkoxy radicals; or
c) a $C_5$-$C_{12}$ aryl group optionally substituted with one or more hydroxyls and/or with one or more $C_1$-$C_5$ alkoxy radicals; and
$R_3$ denotes a radical chosen from:
a) a hydrogen atom; or
b) a saturated linear $C_1$-$C_{10}$ or branched $C_3$-$C_{10}$ alkyl group;
ii) at least two or more natural emulsifiers; and
wherein the oil-in-water cosmetic composition is physically stable.

2. The composition of claim 1 in which radical:
$R_1$ of formula (I) and (I') represents a hydrogen atom, or
$R_1$ of formula (I) and (I') represents a linear $C_1$-$C_{10}$alkyl group or branched $C_3$-$C_{10}$alkyl group.

3. The composition of claim 1 in which:
$R_2$ of formula (I) and (I') represents a hydrogen atom; or
$R_2$ of formula (I) and (I') represents a linear $C_1$-$C_{10}$alkyl group or branched $C_3$-$C_{10}$ alkyl group.

4. The composition of claim 1 in which radical:
$R_2$ of formula (I) and (I') represents a linear $C_1$-$C_{10}$alkyl group or branched $C_3$-$C_{10}$alkyl group.

5. The composition of claim 1 in which radical:
$R_2$ of formula (I) and (I') represents a $C_3$-$C_8$cycloalkyl group;
or
$R_2$ of formula (I) and (I') represents a $C_5$-$C_{12}$ aryl group optionally substituted with one or more hydroxyls and/or with one or more $C_1$-$C_8$ alkoxy radicals.

6. The composition of claim 1 in which:
$R_3$ of formula (I) and (I') represents a hydrogen atom; or
$R_3$ of formula (I) and (I') represents a saturated linear $C_1$-$C_{10}$ or branched $C_3$-$C_{10}$ alkyl group.

7. The composition of claim 1 in which:

$R_1$ of formula (I) and (I') represents a radical chosen from:
a) a hydrogen atom; or
b) a saturated linear $C_1$-$C_6$ or branched $C_3$-$C_6$ alkyl group optionally substituted with one or more groups, which may be identical or different, chosen from:
 i) —O—$R_3$; or
 ii) —S—$R_3$;

$R_2$ of formula (I) and (I') represents a radical chosen from:
a) a hydrogen atom; or
b) a saturated hydrocarbonated group linear $C_1$-$C_{10}$ or branched $C_3$-$C_{10}$ or cyclic $C_3$-$C_8$, optionally substituted with one or more groups, which may be identical or different, chosen from:
 i) —O—$R_3$
 ii) —SR-$_3$
 iii) —C(O) —O—$R_3$; or
 iv) a phenyl group optionally substituted with one or more hydroxyls and/or with one or more $C_1$-$C_4$ alkoxy radicals methoxy;

$R_3$ of formula (I) and (I') represents a radical chosen from:
a) a hydrogen atom; or
b) a saturated linear $C_1$-$C_6$ or branched $C_3$-$C_6$ alkyl group.

8. The composition of claim 1 in which one or more compounds of formula (I), are one or more of compounds 1 to 24 their tautomer, salts, optical isomers, racemates, solvates or a mixture thereof:

| No. | Structure | Chemical name |
|---|---|---|
| 1 | 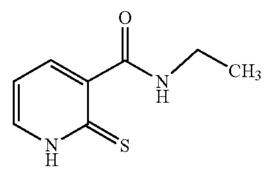 | N-ethyl-2-thioxo-1,2-dihydropyridine-3-carboxamide |
| 2 | 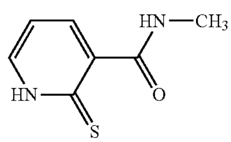 | N-methyl-2-thioxo-1,2-dihydropyridine-3-carboxamide |
| 3 | 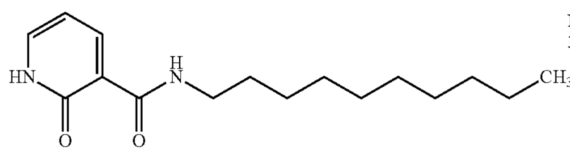 [SMILES: CCCCCCCCCCNC(=O)c1ccc[nH]c1=O] | N-octyl-2-thioxo-1,2-dihydropyridine-3-carboxamide |
| 4 | 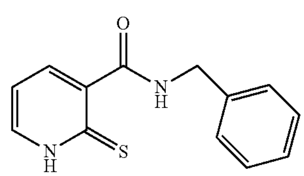 [SMILES: O=C(NCc1ccccc1)c1ccc[nH]c1=S] | N-benzyl-2-thioxo-1,2-dihydropyridine-3-carboxamide |
| 5 | 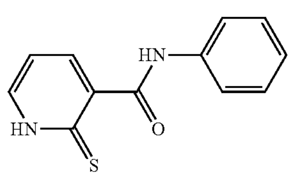 [SMILES: O=C(Nc1ccccc1)c1ccc[nH]c1=S] | N-phenyl-2-thioxo-1,2-dihydropyridine-3-carboxamide |
| 6 | 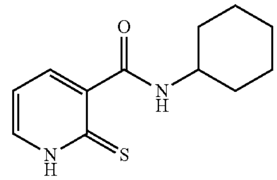 [SMILES: O=C(NC1CCCCC1)c1ccc[nH]c1=S] | N-cyclohexyl-2-thioxo-1,2-dihydropyridine-3-carboxamide |
| 7 | 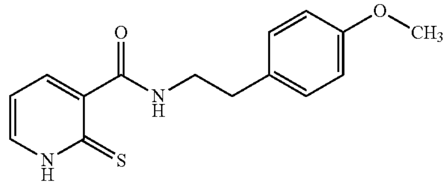 [SMILES: COc1ccc(CCNC(=O)c2ccc[nH]c2=S)cc1] | N-[2-(4-methoxyphenyl)ethyl]-2-thioxo-1,2-dihydropyridine-3-carboxamide |

-continued

| No. | Structure | Chemical name |
|---|---|---|
| 8 | 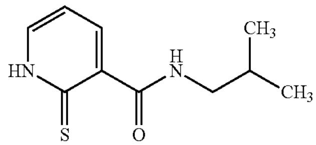 | N-(2-methylpropyl)-2-thioxo-1,2-dihydropyridine-3-carboxamide |
| 9 | 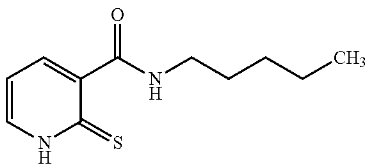 | N-pentyl-2-thioxo-1,2-dihydropyridine-3-carboxamide |
| 10 | 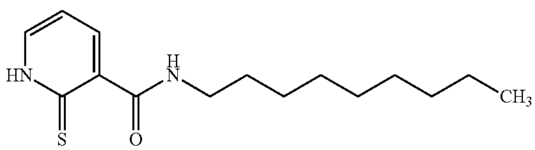 [SMILES: CCCCCCCCCNC(=O)c1ccc[nH]c1=S] | N-nonyl-2-thioxo-1,2-dihydropyridine-3-carboxamide |
| 11 | 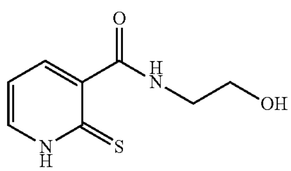 [SMILES: O=C(NCCO)c1ccc[nH]c1=S] | N-(2-hydroxyethyl)-2-thioxo-1,2-dihydropyridine-3-carboxamide |
| 12 | 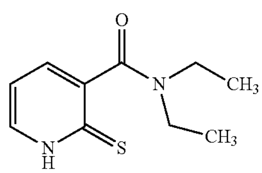 | N,N-diethyl 2-mercaptonicotinamide |
| 13 | 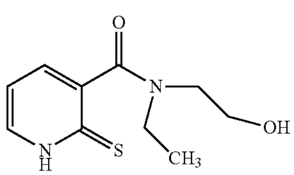 | N-ethyl-N-(2-hydroxyethyl)-2-thioxo-1,2-dihydropyridine-3-carboxamide |
| 14 | 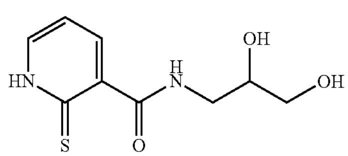 [SMILES: O=C(NCC(O)CO)c1ccc[nH]c1=S] | N-(2,3-dihydroxypropyl)-2-thioxo-1,2-dihydropyridine-3-carboxamide |
| 15 | 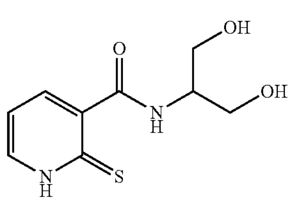 [SMILES: O=C(NC(CO)CO)c1ccc[nH]c1=S] | N-(1,3-dihydroxypropan-2-yl)-2-thioxo-1,2-dihydropyridine-3-carboxamide |
| 16 | 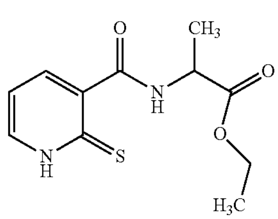 [SMILES: CCOC(=O)C(C)NC(=O)c1ccc[nH]c1=S] | Ethyl N-[(2-thioxo-1,2-dihydropyridin-3-yl)carbonyl]alaninate |

-continued

| No. | Structure | Chemical name |
| --- | --- | --- |
| 17 | 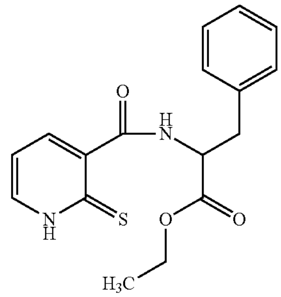 [SMILES: CCOC(=O)C(Cc1ccccc1)NC(=O)c1ccc[nH]c1=S] | Ethyl N-[(2-thioxo-1,2-dihydropyridin-3-yl)carbonyl]phenyl-alaninate |
| 18 | 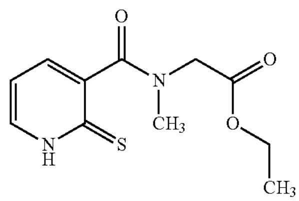 [SMILES: CCOC(=O)CN(C)C(=O)c1ccc[nH]c1=S] | Ethyl N-methyl-N-[(2-thioxo-1,2-dihydropyridin-3-yl)carbonyl]glycinate |
| 19 | 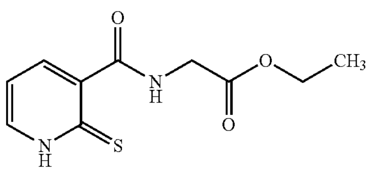 [SMILES: CCOC(=O)CNC(=O)c1ccc[nH]c1=S] | Ethyl N-[(2-thioxo-1,2-dihydropyridin-3-yl)carbonyl]glycinate |
| 20 | 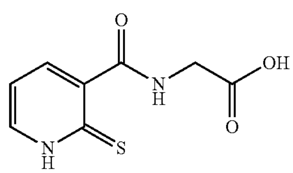 [SMILES: O=C(O)CNC(=O)c1ccc[nH]c1=S] | N-[(2-thioxo-1,2-dihydropyridin-3-yl)carbonyl]glycine |
| 21 | 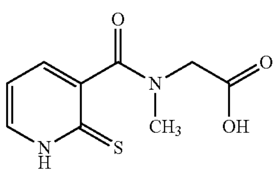 | N-methyl-N-[(2-thioxo-1,2-dihydropyridin-3-yl)carbonyl]glycine |
| 22 | 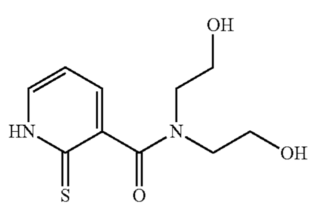 [SMILES: O=C(c1ccc[nH]c1=S)N(CCO)CCO] | N,N-bis(2-hydroxyethyl)-2-thioxo-1,2-dihydropyridine-3-carboxamide |
| 23 | 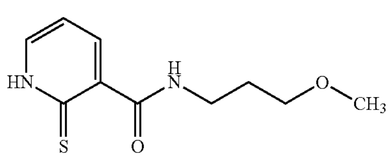 | N-(3-methoxypropyl)-2-thioxo-1,2-dihydropyridine-3-carboxamide |
| 24 | 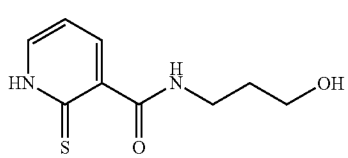 [SMILES: O=C(NCCCO)c1ccc[nH]c1=S] | N-butyl-2-thioxo-1,2-dihydropyridine-3-carboxamide. |

9. The composition of claim 1, wherein the compound i) is present from about 0.01 to about 10 wt. %, based on the total weight of the cosmetic composition.

10. The composition of claim 1, wherein the at least two or more natural emulsifiers ii) is a blend of natural emulsifiers having a HLB from about 10 to about 15.

11. The composition of claim 1, wherein the at least two or more natural emulsifiers ii) has a HLB from about 10 to about 15.

12. The composition of claim 1, wherein the at least two or more natural emulsifiers ii) is selected from the group consisting of inulin lauryl carbamate, C12-20 alkyl glucoside, cetearyl alcohol (and) cetearyl glucoside, Alkyl polyglycosides (APGs), arachidyl alcohol (and) behenyl alcohol (and) arachidyl glucoside, polyglyceryl-3 methylglucose distearate, glyceryl citrate stearate, sucrose and glucose esters and ethers, amino acid-based emulsifier, hydrogenated lecithin, lecithins, sodium lauroyl glutamate, sodium stearoyl glutamate and a mixture thereof.

13. The composition of claim 1, wherein the at least two or more natural emulsifiers ii) is present from about 0.5 to about 6 wt. %, based on the total weight of the cosmetic composition.

14. The composition of claim 1, wherein the oil-in-water cosmetic composition has a low viscosity.

15. The composition of claim 1, wherein the pH is from about 4.5 to about 6.5.

16. An oil-in-water cosmetic composition comprising:
i) from about 0.01 to about 10 wt. % of at least one compound selected from a compound of formula (I) a tautomer of formula (I'), their salts, their optical isomers, racemates, solvates or a mixture thereof:

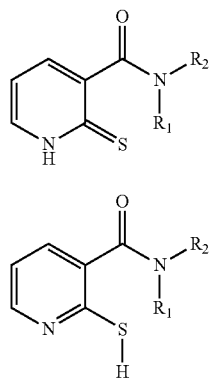

wherein Formulas (I) and (I'):
$R_1$ denotes a radical chosen from:
a) a hydrogen atom; or
b) a saturated linear $C_1$-$C_{10}$ or branched $C_3$-$C_{10}$ alkyl group optionally substituted with one or more groups, which may be identical or different, chosen from:
   i) —O—$R_3$; or
   ii) —S—$R_3$;

$R_2$ denotes a radical chosen from:
a) a hydrogen atom;
b) a saturated hydrocarbonated group linear $C_1$-$C_{12}$ or branched $C_3$-$C_{12}$ or cyclic $C_3$-$C_8$, optionally substituted with one or more groups, which may be identical or different, chosen from:
   i) —O—$R_3$
   ii) —S—$R_3$; or
   iii) —C(O)—O—$R_3$;
iv) a $C_5$-$C_{12}$ aryl group optionally substituted with one or more hydroxyls and/or with one or more $C_1$-$C_5$ alkoxy radicals; or
c) a $C_5$-$C_{12}$ aryl group optionally substituted with one or more hydroxyls and/or with one or more $C_1$-$C_5$ alkoxy radicals; and $R_3$ denotes a radical chosen from:
a) a hydrogen atom; or
b) a saturated linear $C_1$-$C_{10}$ or branched $C_3$-$C_{10}$ alkyl group;

ii. about 0.5 to about 2 wt. % of at least two or more natural emulsifiers that are elected from the group consisting of inulin lauryl carbamate, C12-20 alkyl glucoside, cetearyl alcohol (and) cetearyl glucoside, Alkyl polyglycosides (APGs)

jj, arachidyl alcohol (and) behenyl alcohol (and) arachidyl glucoside, polyglyceryl-3 methylglucose distearate, glyceryl citrate stearate, sucrose and glucose esters and ethers, amino acid-based emulsifier, hydrogenated lecithin, lecithins, sodium lauroyl glutamate, sodium stearoyl glutamate and a mixture thereof;

wherein the weight percentages are based on the total weight of the cosmetic composition.

17. A method for treating skin comprising applying the cosmetic composition of claim 1 or 16 to the skin.

18. A non-therapeutic cosmetic process for depigmenting, lightening and/or bleaching keratin materials comprising the step of:
applying to the keratin substance the composition according to any one of claims 1 to 16.

19. The composition of claim 1 wherein one or more compounds of formula (I) is compound 20:

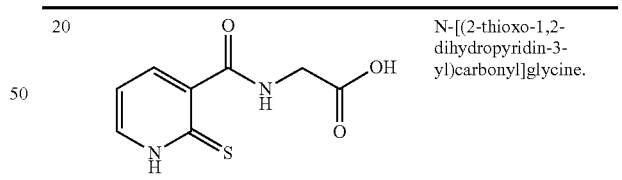

* * * * *